(12) United States Patent
Giuliani et al.

(10) Patent No.: US 9,738,682 B2
(45) Date of Patent: Aug. 22, 2017

(54) COMPOUNDS WITH A COMBINED ANTIOXIDANT ACTIVITY AGAINST FREE RADICALS TOGETHER WITH AN ANTI-INFLAMMATORY ACTION, AND PHARMACEUTICAL AND COSMETIC COMPOSITIONS CONTAINING THEM FOR THE TREATMENT OF SKIN AND HAIR

(71) Applicant: GIULIANI S.P.A., Milan (IT)

(72) Inventors: Giammaria Giuliani, Milan (IT); Anna Benedusi, Milan (IT); Barbara Marzani, Carbonara Al Ticino (IT); Sergio Baroni, Villa D'Adda (IT); Elena Pini, Milan (IT); Raffaella Gandolfi, Milan (IT)

(73) Assignee: Giuliani S.p.A., Milan (IT)

( * ) Notice: Subject to any disclaimer, the term of this patent is extended or adjusted under 35 U.S.C. 154(b) by 0 days.

(21) Appl. No.: 15/124,273

(22) PCT Filed: Mar. 10, 2015

(86) PCT No.: PCT/EP2015/054934
§ 371 (c)(1),
(2) Date: Sep. 7, 2016

(87) PCT Pub. No.: WO2015/135927
PCT Pub. Date: Sep. 17, 2015

(65) Prior Publication Data
US 2017/0015700 A1 Jan. 19, 2017

(30) Foreign Application Priority Data
Mar. 10, 2014 (IT) ............... MI2014A0368

(51) Int. Cl.
| | | |
|---|---|---|
| *C07J 9/00* | (2006.01) |
| *A61K 8/36* | (2006.01) |
| *A61Q 5/00* | (2006.01) |
| *A61K 45/06* | (2006.01) |
| *C07C 69/587* | (2006.01) |
| *C07C 279/14* | (2006.01) |
| *C07C 57/03* | (2006.01) |
| *A61K 8/37* | (2006.01) |
| *A61K 8/44* | (2006.01) |
| *A61Q 1/14* | (2006.01) |
| *A61K 8/63* | (2006.01) |
| *A61Q 7/00* | (2006.01) |
| *A61Q 17/04* | (2006.01) |
| *A61Q 19/00* | (2006.01) |

(52) U.S. Cl.
CPC ............. *C07J 9/00* (2013.01); *A61K 8/361* (2013.01); *A61K 8/37* (2013.01); *A61K 8/375* (2013.01); *A61K 8/44* (2013.01); *A61K 8/63* (2013.01); *A61K 45/06* (2013.01); *A61Q 1/14* (2013.01); *A61Q 5/00* (2013.01); *A61Q 7/00* (2013.01); *A61Q 17/04* (2013.01); *A61Q 19/00* (2013.01); *A61Q 19/004* (2013.01); *A61Q 19/007* (2013.01); *C07C 57/03* (2013.01); *C07C 69/587* (2013.01); *C07C 279/14* (2013.01); *A61K 2800/10* (2013.01)

(58) Field of Classification Search
CPC ........ C07J 9/00; C07C 69/587; C07C 279/14; C07C 57/03
See application file for complete search history.

(56) References Cited

U.S. PATENT DOCUMENTS 2,462,337 A    2/1949   Schechter

FOREIGN PATENT DOCUMENTS

| EP | 2407163 A1 | 1/2012 |
| WO | 2011/132177 A1 | 10/2011 |

OTHER PUBLICATIONS

Ohta et al, Insect Biochemistry and Molecular Biology (2000),30(10), 947-952.*
International Search Report and Written Opinion for corresponding Application No. PCT/EP2015/054934 (Jun. 23, 2015).
International Preliminary Report on Patentability for corresponding Application No. PCT/EP2015/054934 (Apr. 15, 2016).

* cited by examiner

*Primary Examiner* — Sudhakar Katakam
(74) *Attorney, Agent, or Firm* — LeClairRyan, a Professional Corporation

(57) ABSTRACT

The invention relates to 2,4,6-octatrienoic acid derivative compounds having general formula (I) $(CH_3-CH=CH-CH=CH-CH=CH-CO-O-)_n-R$ (I) consisting of esters wherein n=1, 2, 3 and wherein R is selected from alkyl, aryl or cycloalkyl of a polyol, phenol or phenolic acid; or consisting of a salt wherein n=1 and R=arginine, as active ingredients in a pharmaceutical or cosmetic composition having a combined antioxidant activity against free radicals together with an anti-inflammatory action.

11 Claims, 1 Drawing Sheet

COMPOUNDS WITH A COMBINED ANTIOXIDANT ACTIVITY AGAINST FREE RADICALS TOGETHER WITH AN ANTI-INFLAMMATORY ACTION, AND PHARMACEUTICAL AND COSMETIC COMPOSITIONS CONTAINING THEM FOR THE TREATMENT OF SKIN AND HAIR

This application is a national stage application under 35 U.S.C. §371 of PCT Application No. PCT/EP2015/054934, filed Mar. 10, 2015, which claims priority of Italy Application No. MI2014A000368, filed Mar. 10, 2014, which are hereby incorporated by reference in their entirety.

FIELD OF THE INVENTION

Object of the present invention are compounds with antioxidant activity against free radicals, which are useful as active ingredients for the preparation of pharmaceutical or cosmetic compositions for the treatment of skin and hair.

BACKGROUND ART

Oxygen is an essential element for the life of all aerobic organisms. However, since oxygen is metabolized in animal tissues by subsequent reductions to superoxide anion, hydrogen peroxide and hydroxyl radical, these metabolites represent a potential threat to the living organisms themselves. These different metabolites are known as reactive oxygen species (ROS).

At low concentrations, the ROS play essential intracellular functions acting, for example, as second messengers, gene regulators, and mediators of cellular activation (kinases and transcription factors). They also play a key role in the defense against infectious agents and they are modulators in the process of cell death, both apoptosis and necrosis.

When ROS levels are high and the cellular systems are no longer able to eliminate them, an imbalance between ROS and antioxidants occurs that is known as oxidative stress.

The oxidative stress is detrimental both for the cells and for the extracellular matrix, the nuclear and mitochondrial DNA, the membrane lipids, and the proteins.

Specifically, the DNA damage (single-stranded lesions, bases deletions, or "cross-linking" between DNA and proteins) forms the basis for UV-induced skin carcinogenesis, while the lipid peroxidation affects the phospholipids both from a structural and a functional point of view, thus leading to rigidity and permeability of cell membranes.

Changes at the protein level, both direct and activated by proteases, are reflected on the skin as an alteration of collagen and elastin.

Furthermore, the excessive production of ROS can induce mitochondrial damage, leading to a sharp reduction of ATP and cell death due to necrosis.

The skin is constantly influenced by environmental factors and, specifically, by UV rays. In the skin, the free radicals produced by UV radiation can cause damage to the cellular structures (DNA, proteins) and destabilize the keratinocytes membranes, resulting in premature aging of skin cells.

Particularly when exposed to UV radiation, the skin undergoes alterations resulting in inflammatory phenomenons, photo-aging, and skin diseases.

Photo-aging is accompanied by the appearance of wrinkles, loss of elasticity, increased fragility of the skin and a slower healing process.

In order to avoid ROS induced damage, by maintaining the balance in their production, the tissues are equipped with antioxidant systems that inhibit ROS production through a direct "scavenging", decrease the amount of oxidizing agents inside and outside the cells, prevent ROS from reaching their biological targets, limit the propagation of oxidizing agents as occurs during lipid peroxidation, and counteract the oxidative stress thereby preventing aging.

In WO2011/132177 the same Applicant describes the use of 2,4,6-octatrienoic acid, and some derivatives thereof, as endowed with a remarkable antioxidant activity measured in tests of inhibition of LPS-induced ROS and in tests of lipid peroxidation induced by TBT, using Trolox, a known derivative of vitamin E, as a positive control.

SUMMARY OF THE INVENTION

It has now surprisingly been found, and this is the object of the present invention, that a different group of 2,4,6-octatrienoic acid derivatives have a high antioxidant activity against free radicals, accompanied also by a significant anti-inflammatory activity.

Such compounds according to the invention are 2,4,6-octatrienoic acid derivatives of general formula (I)

$$(CH_3-CH=CH-CH=CH-CH=CH-CO-O-)_n-R \quad (I)$$

consisting of esters wherein n=1, 2, 3, and wherein R is selected from alkyl, aryl or cycloalkyl of a polyol, phenol or phenolic acid, preferably selected from glycerol, sitosterol, resveratrol, caffeic acid, ferulic acid, gallic acid; or consisting of a salt wherein n=1 and R=arginine.

DETAILED DESCRIPTION OF THE INVENTION

Preferred compounds according to the present invention are summarized in the Table I below:

TABLE 1

| Compound No. | Structure | Name |
|---|---|---|
| (1) | 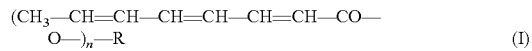 | Caffeic acid 3,4-di-octatrienoate |

TABLE 1-continued

| Compound No. | Structure | Name |
|---|---|---|
| (2) | 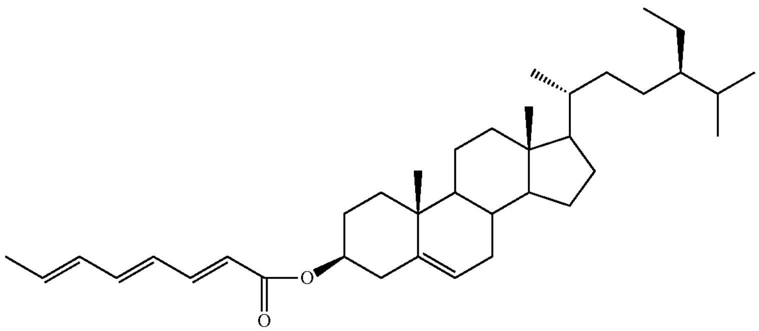 [SMILES: C/C=C/C=C/C=C/C(=O)O[C@H]1CC[C@@]2(C)C(=CCC3C4CCC([C@H](C)CC[C@@H](CC)C(C)C)[C@@]4(C)CCC32)C1] | Sitosterol octatrienoate |
| (3) | OPPURE | Resveratrol octatrienoate (two isomers) |
| (4) | 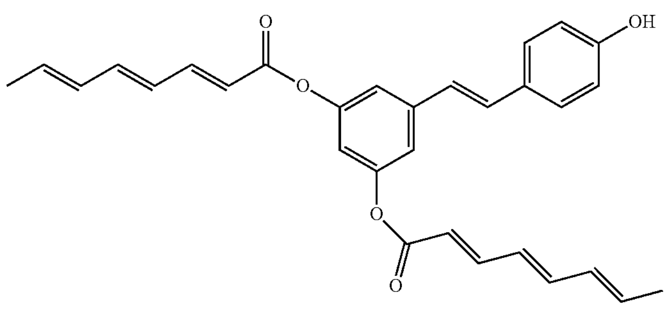 [SMILES: C/C=C/C=C/C=C/C(=O)Oc1cc(/C=C/c2ccc(O)cc2)cc(OC(=O)/C=C/C=C/C=C/C)c1] | Resveratrol 3,5-di-octatrienoate |
| (5) | 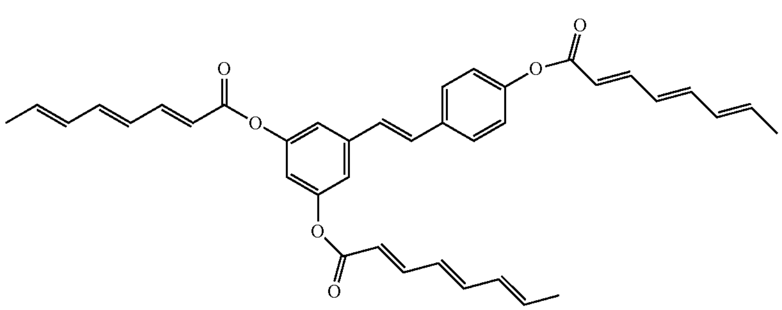 [SMILES: C/C=C/C=C/C=C/C(=O)Oc1ccc(/C=C/c2cc(OC(=O)/C=C/C=C/C=C/C)cc(OC(=O)/C=C/C=C/C=C/C)c2)cc1] | Resveratrol tri-octatrienoate |

TABLE 1-continued

| Compound No. | Structure | Name |
|---|---|---|
| (6) | 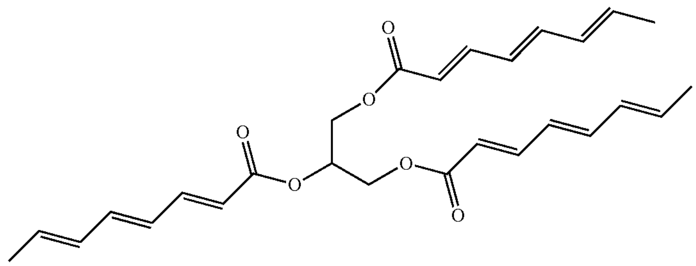 [SMILES: C/C=C/C=C/C=C/C(=O)OCC(COC(=O)/C=C/C=C/C=C/C)OC(=O)/C=C/C=C/C=C/C] | Glycerol tri-octatrienoate |
| (7) | 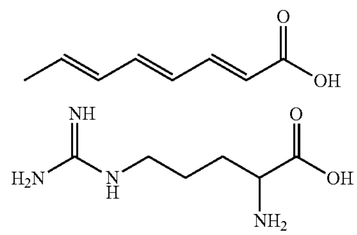 | Octatrienoic acid arginine salt |
| (8) | 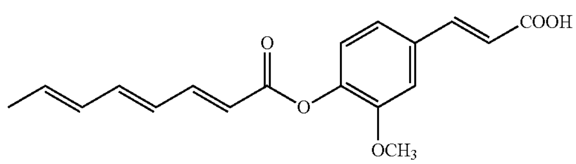 [SMILES: C/C=C/C=C/C=C/C(=O)Oc1ccc(/C=C/C(=O)O)cc1OC] | Ferulic acid octatrienoate |
| (9) | 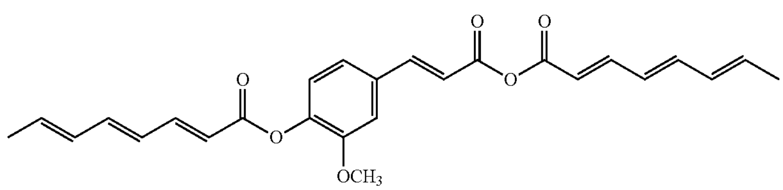 [SMILES: C/C=C/C=C/C=C/C(=O)OC(=O)/C=C/c1ccc(OC(=O)/C=C/C=C/C=C/C)c(OC)c1] | Octatrienoic ferulic 4-(2,4,6-octatrienoyl) anhydride |
| (10) | 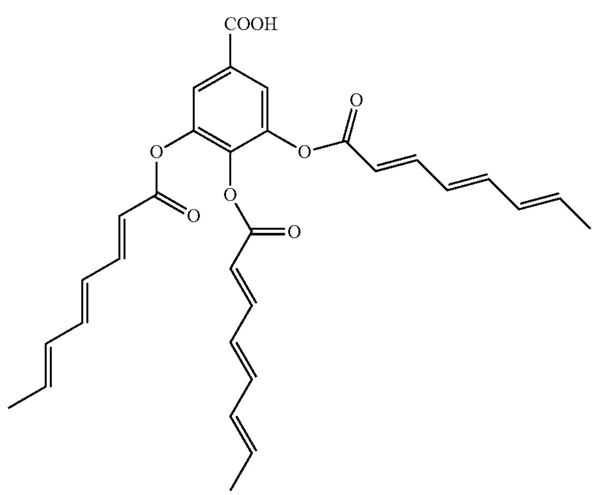 [SMILES: C/C=C/C=C/C=C/C(=O)Oc1cc(C(=O)O)cc(OC(=O)/C=C/C=C/C=C/C)c1OC(=O)/C=C/C=C/C=C/C] | Gallic acid tri-octatrienoate |

Object of the present invention are:
the compounds of general formula (I) defined above;
their use in therapeutics and cosmetics for topical application on the skin or the scalp for obtaining an antioxidant activity against ROS combined with an antiinflammatory action, for opposing at the same time the oxidizing action and the inflammatory effects of free radicals, and preserving thereby the physiological conditions of human epidermis and preserving the physiological conditions of the hair, thus their state of health;
the compositions for therapeutic and cosmetic use comprising said compounds of general formula (I) as active ingredients, alone or in combination with one or more of the others, formulated with excipients for topical use suitable for local administration to the epidermis or the scalp.

According to the invention, a composition comprising as active ingredient one or more compounds of general formula (I) in an amount in the range between 0.5 µM and 0.1 mM is preferred.

Preferred ranges of active ingredient amounts in the composition, expressed as parts by weight, w/w (%), are for examples: 0.01-2.5; 0.1-2.5; 0.2-2.5; 0.01-1.5; 0.1-2; 0.2-2; 0.03-3; 0.2-4.

Non limiting examples of preparation of the preferred compounds of the invention according the Table I above, are reported below.

In general, the synthesis involves the initial conversion of 2,4,6-octatrienoic acid in more reactive derivatives thereof, such as the chloride or the anhydride. All the reactions are carried out under anhydrous conditions, with the glassware kept overnight in an oven at 80° C., under a nitrogen atmosphere, and using dry solvents (Aldrich). Each synthesized compound was characterized by IR spectroscopy, NMR (1H and 13C), and mass analysis.

IR analysis: the samples to be analyzed, when liquids have been placed as such between two sodium chloride glasses, when solids were mixed with KBr in the ratio 1:100, and analyzed using a SpectrumOne FT-IR (Perkin Elmer) instrument.

NMR Analysis: the samples were dissolved in $CDCl_3$ or DMSO, depending on their solubility, and analyzed with a Varian Mercury Plus 200 instrument operating at 200 MHz associated with the Sun program, or with a Bruker Avance 500, operating at 500 MHz and associated with the program Bruker X-Win Nmr vers. 3.0.

Mass Analysis: the spectra were obtained with a mass spectrometer, Thermo Finnigan LCQ Advantage, equipped with an electrospray ionization source (ESI) and an ion trap analyzer. The samples were dissolved in a suitable solvent and injected directly into the ionization chamber. Spectra in positive or negative ion mode were obtained, depending on the sensitivity of the sample.

Synthesis of Caffeic Acid 3,4-Di-Octatrienoate (3,4-Di-octatrienoyl Caffeic Acid), Compound (1)

284 mg (0.632 mmoli) of caffeic acid and a catalytic amount (30 mg) of DMAP in 3.5 ml of dry pyridine are placed under magnetic stirring. While keeping in an ice bath, once the temperature has reached 0° C., 300 mg (1.162 mmoli) of octatrienoic acid anhydride are added to the mixture in small portions Once this addition is complete, the mixture is brought back to room temperature and kept under a nitrogen atmosphere and magnetic stirring for 12 h, protected from the light.

20 ml of $H_2O$ are added and the mixture is extracted with 20 ml of $CH_2Cl_2$. The organic phase is washed with 15 ml of 1N HCl, and then with $H_2O$. The organic phase is dried over $Na_2SO_4$, filtered and evaporated. Recrystallization from methanol.

TLC control: hexane/acetone (1:1).
$C_{25}H_{24}O_6$
PM 420.3

Synthesis of Sitosterol Octatrienoate (β-Sitosterol-2,4,6-Octatrienoate), Compound (2)

500 mg (1.21 mmoli) of sitosterol and 628.93 mg (5.148 mmoli) of DMAP (dimethylaminopyridine) in 10 ml of dry toluene are placed under magnetic stirring. While keeping in an ice bath, a solution consisting of 497 mg (3.6 mmoli) of 2,4,6 octatrienoyl chloride in 10 ml of dry toluene is added dropwise at 0° C. The mixture is kept under magnetic stirring at room temperature for 24 hours, protected from the light. The reaction mixture is filtered and the filtrate is washed with saturated aqueous $NaHCO_3$, and then with $H_2O$. The organic phase is dried over $Na_2SO_4$, filtered and evaporated.

TLC control: hexane/ethyl acetate/diethyl ether 5:2:1
$C_{37}H_{58}O_2$
PM 534.89

Synthesis of Resveratrol Di-Octatrienoate, [3,5 (Di-2,4,6 Octatrienoyl) Resveratrol], Compound (4)

100 mg (0.170 mmoli) of 2,4,6-octatrienoyl resveratrol in 20 ml of tert butyl methyl ether are placed under magnetic stirring, and 500 mg of *candida rugosa* and 200 µl of $H_2O$ are added to it. The mixture is kept under magnetic stirring at 35° C. for 24 hours.

The reaction mixture is filtered and the solution is washed with 15 ml of saturated aqueous $NaHCO_3$, and then with $H_2O$. The organic phase is dried over $Na_2SO_4$, filtered and evaporated.

TLC control: hexane/AcOEt 1:1.
$C_{30}H_{28}O_5$
PM: 468

Synthesis of Resveratrol Tri-Octatrienoate, [2,4,6-Trioctatrienoyl Resveratrol], Compound (5)

250 mg (1.096 mmoli) of resveratrol and 430 µl of TEA (3.10 mmoli, 313 mg) in 20 ml of dry chloroform, non-stabilized with ethanol, are placed under magnetic stirring. While keeping in an ice bath, once the temperature has reached 0° C., a solution consisting of 3.60 mmoli of octatrienoic acyl chloride (obtained starting from 500 mg, 3.6 mmol of acid) in 6 ml of dry chloroform, non-stabilized with ethanol, is added to the mixture dropwise.

Once this addition is complete, the mixture is brought back to room temperature and kept under a nitrogen atmosphere and magnetic stirring for 12 h, protected from the light.

The formed TEA salts are filtered off, and the solution is extracted with 15 ml of saturated aqueous $NaHCO_3$, and then with 15 ml of water.

The organic phase is dried over $Na_2SO_4$, filtered and evaporated.

TLC control: hexane/acetone (1:1).
$C_{70}H_{104}O_6$
PM 588.89

Synthesis of Glycerol Tri-Octatrienoate, (Gliceryl-2,4,6-Octatrienoate), Compound (6)

52 µl (0.71 mmoli) of glycerol in 20 ml of dry $CHCl_3$, non-stabilized with ethanol, are placed under magnetic stirring. While keeping in an ice bath, once the temperature has reached 0° C., 260 mg (2.13 mmoli) of DMAP and 550 mg (2.118 mmoli) of octatrienoic acid anhydride are added to the mixture in small portions.

Once this addition is complete, the mixture is brought back to room temperature and kept under a nitrogen atmosphere and magnetic stirring for 4 h, and then at 40° C. for 2 hours, protected from the light.

The reaction mixture is washed with 15 ml of saturated aqueous $NaHCO_3$, and then with $H_2O$. The organic phase is dried over $Na_2SO_4$, filtered and evaporated. Purification by column chromatography on silica gel (ratio raw product/silica 1:30) eluting with a mixture hexane/AcOEt 7:3.
$C_{27}H_{32}O_6$
PM: 452.61

Preparation of Octatrienoic Acid L-Arginine Salt, Compound (7)

0.63 g (3.6 mmoli) of L-arginine are dissolved in a mixture consisting of 43 ml of methanol and 15 ml of $H_2O$. 0.5 g (3.6 mmoli) of octatrienoic acid in 29 ml, are placed under magnetic stirring, protected from the light; when the dissolution is complete, the L-arginine solution is slowly added to it and the mixture is kept under magnetic stirring at room temperature for 24 hours. After evaporation, if necessary, the obtained solid is triturated in acetonitrile.

TLC control: AcOEt/MeOH/TEA 8:2:0.2

Synthesis of Ferulic Acid Octatrienoate, [4-(2,4,6-Octatrienoyl) Ferulic Acid], Compound (8)

240 mg (1.24 mmoli) of ferulic acid and 150 mg (1.24 mmoli) of DMAP in 25 ml of dry toluene are placed under magnetic stirring. While keeping in an ice bath, once the temperature has reached 0° C., 351 mg (1.36 mmoli) of octatrienoic acid anhydride in 10 ml of dry toluene are added to the mixture.

Once this addition is complete, the mixture is brought back to room temperature and kept under a nitrogen atmosphere and magnetic stirring for 12 h, protected from the light.

After filtering under vacuum the DMAP salts, the solution is evaporated; the evaporation residue is resumed with 20 ml of ethyl acetate, washed with 20 ml of 1N HCl, with 20 ml of $H_2O$, and then with saturated aqueous $NaHCO_3$ (2×20 ml). The organic phase is dried over $Na_2SO_4$, filtered and evaporated.

TLC control: ethyl acetate/hexane (7:3).

$C_{18}H_{18}O_5$

PM 314

Synthesis of Octatrienoic Ferulic 4-(2,4,6-Octatrienoyl) Anhydride, Compound (9)

500 mg (2.57 mmoli) of ferulic acid in 25 ml of dry toluene are placed under magnetic stirring. While keeping in an ice bath, once the temperature has reached 0° C., 715.5 µl of TEA (5.15 mmoli), and then a solution consisting of 5.15 mmoli octatrienoic acid acyl chloride (obtained starting from 711.6 mg, 5.15 mmol of acid) in 10 ml of dry toluene, are added the mixture dropwise.

Once this addition is complete, the mixture is brought back to room temperature and kept under a nitrogen atmosphere and magnetic stirring for 1 h, protected from the light.

The formed TEA salts are filtered off, and the solution is extracted with 15 ml of saturated aqueous $NaHCO_3$, and then with 15 ml of water. The organic phase is dried over $Na_2SO_4$, filtered and evaporated.

TLC control: Ethyl acetate 100%.

Yield: 20%

$C_{26}H_{26}O_6$

PM: 434

Synthesis of Gallic Acid Tri-Octatrienoate, [3,4,5-(2,4,6 Octatrienoyl) Gallic Acid], Compound (10)

200 mg (1.18 mmoli) of gallic acid and 440 mg (3.54 mmoli) of DMAP in 30 ml of dry dioxane are placed under magnetic stirring. While keeping in an ice bath, once the temperature has reached 15° C., 913.32 mg (3.54 mmoli) of octatrienoic acid anhydride are added to the mixture, in small portions.

Once this addition is complete, the mixture is brought back to room temperature and kept under a nitrogen atmosphere and magnetic stirring for 12 h, protected from the light.

The solution is evaporated; the evaporation residue is resumed with 20 ml of dichloromethane, washed with 20 ml of 1N HCl, with 20 ml×2 of $H_2O$, and then with saturated aqueous $NaHCO_3$ (2×20 ml). The organic phase is dried over $Na_2SO_4$, filtered and evaporated.

TLC control: ethyl acetate 100%.

$C_{31}H_{30})_8$

PM: 530

EXAMPLES

The following are formulation examples, not to be intended as limiting, of compositions according to the invention particularly suitable for topical application on the skin or the hair to obtain, particularly, the effect specified herein (UV protection, hair loss prevention, etc.).

The amounts of the components, identified herein according to INCI nomenclature, are expressed as percentage by weight in the described ranges:

Example 1

Medium Protection Sunscreen

| Component (INCI name) | Amount w/w (%) |
|---|---|
| C12-15 alkyl benzoate | 5-7 |
| Ethylhexyl methoxycinnamate | 3-7 |
| Isostearyl isostearate | 2-8 |
| Styrene/Acrylates Copolymer | 1-5 |
| Acrylates/C10-30 Alkyl Acrylate Cross polymer | 0.05-0.7 |
| Butylene glycol cocoate | 1-5 |
| Butyl methoxydibenzoylmethane | 1-5 |
| Diethylamino Hydroxybenzoyl Hexyl Benzoate | 1-5 |
| Ethylhexyl Triazone | 1-5 |
| Octocrylene | 1-5 |
| Polyurethane-34 | 1-5 |
| PPG-15 stearyl ether | 1-5 |
| Diethylhexyl syringylidene malonate | 0.10-1 |
| Sorbityl furfural | 0.05-0.1 |
| 3,4,5-(2,4,6 octatrienoyl) gallic acid | 0.01-2.5 |
| Quercetin | 0.001-0.005 |
| Ethylhexylglycerin | 0.15-0.6 |
| *Coleus forskohlii* root extract | 0.005-0.5 |
| Polyperfluoroethoxymethoxy Difluoroethyl PEG Phosphate | 0.2-1.50 |
| Parfum | 0.1-0.5 |
| Phenoxyethanol | 0.80-1 |
| Water | 40-60 |
| Sodium Hydroxide | q.s. |

Example 2

Anti-Hair Loss Lotion

| Component (INCI name) | Amount w/w (%) |
|---|---|
| Denatured alcohol | 10-30 |
| Disodium EDTA | 0.025-0.2 |
| 3,5-(di 2,4,6-octatrienoyil) resveratrol | 0.1-2.5 |
| Biotin | 0.001-0.005 |
| Parfum | 0.3 |
| *Ajuga reptans* leaf extract | 0.01-0.05 |
| Calcium pantothenate | 0.05-0.4 |
| PEG-40 Hydrogenated Castor Oil | 0.2-1 |
| Water | q.s. to 100 |

Example 3

Trichological Lotion

| Component | Amount |
|---|---|
| Denatured alcohol | 1-5 |
| Betaine | 0.0075-0.015 |
| Citric acid | 0.01-0.03 |
| Mannitol | 0.01-0.03 |
| 3,5-(di-2,4,6 octatrienoyl) resveratrol | 0.01-2.5 |
| Hydrogenated Castor Oil polyoxyethylenated | 0.01-0.05 |
| Parfum Equador S2611 WAI | 0.03-0.05 |
| VP/VA Copolymer | 0.004-0.01 |
| Water | q.b. a 100 |

Example 4

After Sun Body Milk

| Component (INCI name) | Amount w/w (%) |
|---|---|
| Glycerin | 1-6 |
| Methylpropanediol | 1-6 |
| Cetyl hydroxyethylcellulose | 0.1-0.4 |
| Xanthan gum | 0.1-0.4 |
| Tapioca starch | 1-2 |
| Disodium EDTA | 0.025-0.2 |
| 2,4,6-Trioctatrienoyl resveratrol | 0.2-2.5 |
| Sorbitan stearate | 2-5 |
| Sucrose cocoate | 0.1-1 |
| Ethylhexyl palmitate | 1-5 |
| Hydrogenated polydecene | 1-5 |
| Caprylic/capric triglycerides | 1-5 |
| *Butyrospermum parkii* | 1-5 |
| Meadowfoam (*Limnanthes alba*) seed oil | 1-3 |
| Dimethicone | 1-3 |
| Sodium hydroxymethylglycinate | 0-1-0.2 |
| Phenoxyethanol | 0.7-0.9 |
| Lactic acid | q.b. |
| Parfum | 0.3 |
| Delta tocopherol | 0.02-0.25 |
| Water | q.s. to 100 |

Example 5

Face Cream

| Component (INCI name) | Amount w/w (%) |
|---|---|
| Glycerin | 2-5 |
| Diglycerin | 0.2-2 |
| Cetearyl alcohol | 0.2-2.5 |
| Cetearyl glucoside | 0.2-2.5 |
| PEG-100 Stearate | 0.2-1 |
| Tetrasodium Glutamate Diacetate | 0.1-0.5 |
| 2,4,6-Trioctatrienoyl resveratrol | 0.2-2.5 |
| Palm butter | 0.5-3 |
| Hydrogenated Evening Primrose Oil | 0.5-3 |
| Octyldodecanol | 0.5-3 |
| Hydrogenated castor oil | 1-4 |
| Ethylhexyl cocoate | 1-4 |
| Acrylates/C10-30 Alkyl acrylate crosspolymer | 1-2 |
| *Butyrospermum parkii* | 1-5 |
| Delta tocopherol | 0.05-0.2 |
| Dimethicone | 0.5-1.5 |
| Dimethicone crosspolymer | 0.1-1.5 |
| Ethylhexylglycerin | 0-25-0.5 |
| Phenoxyethanol | 0.5-0.99 |
| Parfum | q.b. |
| Water | q.b. a 100 |

Example 6

Leave-On Make-Up Remover

| Component (INCI name) | Amount w/w (%) |
|---|---|
| Glycerin | 2-5 |
| Ethylhexylglycerin | 0.25-0.5 |
| 4-(2,4,6-octatrienoyil) ferulic acid | 0.01-1.5 |
| Trehalose | 0.5-1 |
| PPG-26 Buteth-26 | 2-15 |
| PEG-40 Hydrogenated Castor Oil | 2-15 |
| Methylpropanediol | 1-6 |
| Water | 60-80 |

Example 7

High Protection Sunscreen

| Component (INCI name) | Amount w/w (%) |
|---|---|
| Ethylhexyl methoxycinnamate | 5-21 |
| Diethylamino Hydroxybenzoyl Hexyl Benzoate | 5-19 |
| C12-15 Alkyl benzoate | 5-20 |
| Mixed decanoyl and octanoyl triglycerides | 5-20 |
| Butylene glycol dicaprylate/dicaprate | 3-10 |
| Micronized titanium dioxide 100Z | 3-10 |
| Ethylhexyl salicylate | 2-8 |
| Isolan GPS | 2-8 |
| Diisopropyl sebacate | 2-8 |
| Ethylhexyl triazone | 2-6 |
| Glyceryl behenate/eicosadioate | 2-6 |
| Cyclopentasiloxane | 1-4 |
| PEG-30 Dipolyhydroxystearate | 1-4 |
| Butyl methoxydibenzoylmethane | 1-3 |
| Silica dimethyl silylate | 1-2 |
| *Calendula* oil extract | 1-2 |
| Caprylyl glycol | 0.1-1 |
| Avocadol | 0.1-1 |
| Shea Butter | 0.1-1 |
| Glicerin | 0.1-1 |
| Magnesium sulfate heptahydrate | 0.1-1 |
| Magnesium stearate (of plant origin) | 0.1-1 |
| Triethyl citrate | 0.1-1 |
| Phenoxyethanol | 0.1-1 |
| Parfum ALF Helianthe M 070344 | 0.1-1 |
| Benzoic acid | 0.1-1 |
| Triclosan | 0.1-1 |
| Dissolvine GL-38 | 0.1-1 |
| Lactic acid 80% sol | 0.1-1 |
| Bis-ethylhexyl hydroxydimethoxy benzylmalonate | 0.1-1 |
| Furalglucitole | 0.1-1 |
| Betaine | 0.1-1 |
| Inositol | 0.1-1 |
| Trehalose dihydrate | 0.1-1 |
| Xylitol | 0.1-1 |
| Beta sitosterol | 0.1-1 |
| Boron nitride | 0.1-1 |
| 18 Beta-Glycyrrhetic acid | 0.05-0.1 |
| Sodium Hydroxide | 0.05-0.1 |
| Taurine | 0.05-0.1 |
| Allantoin | 0.05-0.1 |
| Batyl alcohol | 0.05-0.1 |

-continued

| Component (INCI name) | Amount w/w (%) |
|---|---|
| Hydrogenated soy lecithin | 0.05-0.1 |
| Pentaerythrityl tetra-di-t-butyl hydroxyhydrocinnamate | 0.05-0.1 |
| 3,4-dioctatrienoyl caffeic acid | 0.01-2.5 |
| Water | q.b. a 100 |

Example 8

Face Serum

| Component (INCI name) | Amount w/w (%) |
|---|---|
| Xanthan gum | 0.10-0.20 |
| Sodium hyaluronate | 0.05-1 |
| Inositol | 0.05-1 |
| Xylitol | 0.05-1 |
| Taurine | 0.05-1 |
| Betaine | 0.05-1 |
| C14-22 Alcohols | 0.05-2 |
| C12-20 Alkyl glucoside | 0.05-1 |
| Octyldodecanol | 1-3 |
| Ethylhexyl methoxycinnamate | 0.50-3 |
| Octocrylene | 0.10-3 |
| Butylene glycol | 0.10-5 |
| Glycerin | 1-4 |
| Gliceril-tri-2,4,6-octatrienoate | 0.1-2 |
| Phenoxyethanol | 0.8-1 |
| Sodium hydroxide | 0.001-0.2 |
| Citric acid | 0.001-0.3 |
| Hydroxyethyl acrylate/Sodium acryloyldimethyl Taurate copolymer | 0.01-2 |
| Polyisobutene | 0.01-1.5 |
| PEG-7 Trimethylolpropane Coconut Ether | 0.01-1 |
| Parfum | 0.01-1 |
| Water | q.b..100 |

Example 9

Trichological Lotion

| Component (INCI name) | Amount w/w (%) |
|---|---|
| Alcohol denat | 10-30 |
| Pentylene glycol | 0.025-0.2 |
| Octatrienoic ferulic 4-(2,4,6-octatrienoyl)anhydride | 0.1-2 |
| Parfum | 0.05-0.2 |
| PEG-6 Caprylic/Capric Glycerides | 0.1-1 |
| Water | q.s. to 100 |

Example 10

Sun Oil

| Component (INCI name) | Amount w/w (%) |
|---|---|
| Bis-Ethylhexyloxyphenol Methoxyphenyl Triazine | 1-4 |
| Octyldodecanol | 1-6 |
| Alcohol denat. Type D | 1-15 |
| C12-15 alkyl benzoate | 1-15 |

-continued

| Component (INCI name) | Amount w/w (%) |
|---|---|
| Diethylamino Hydroxybenzoyl Hexyl Benzoate | 1-5 |
| Caprylic/capric Triglyceride | 1-60 |
| Ethylhexyl methoxycinnamate | 0.50-10 |
| Octocrylene | 0.1-5 |
| Simmondsia Chinensis Seed Oil | 0.1-10 |
| Parfum | 0.01-1 |
| Glicerol-tri-2,4,6-octatrienoate | 0.03-3 |

Example 11

Face Cream

| Component (INCI name) | Amount w/w (%) |
|---|---|
| Propanediol | 1-7 |
| Xylitol | 0.3-1 |
| Cetearyl glucoside | 0.1-2 |
| Polyglyceryl-3 Rice Branate | 0.1-3 |
| Cetearyl alcohol | 0.05-1 |
| Disodium EDTA | 0.01-0.1 |
| Beta-sitosterol-2,4,6-octatrienoate | 0.2-2 |
| C12-15 alkyl benzoate | 1-5 |
| Ethylhexyl methoxycinnamate | 0.5-10 |
| Octocrylene | 0.5-5 |
| Butyrospermum parkii butter | 0.5-3 |
| Citric acid | 01-0.3 |
| Simmondsia Chinensis seed oil | 0.1-0.3 |
| Hydrogenated Evening Primrose Oil | 0.5-3 |
| Octyldodecanol | 0.5-3 |
| Caprylic/Capric triglyceride | 1-5 |
| Isostearyl isostearate | 0.1-5 |
| Beta sitosterol | 0.1-0.5 |
| Delta tocopherol | 0.01-0.2 |
| Caprylyl glycol | 0.05-0.5 |
| 1,2 Hexanediol | 0.1-0.7 |
| Sodium hydroxide | 0.001-0.2 |
| Phenoxyethanol | 0.5-1 |
| Parfum | 0.05-0.5 |
| Water | q.s. to 100 |

Example 12

Hair Protective Oil

| Component (INCI name) | Amount w/w (%) |
|---|---|
| Cyclopentasiloxane | 1-50 |
| Alcohol denat. Type C | 1-15 |
| C12-15 alkyl benzoate | 1-10 |
| Ethylhexyl methoxycinnamate | 1-5 |
| Octocrylene | 0.1-0.5 |
| Disiloxane | 1-49 |
| Parfum | 0.05-0.3 |
| Oleyl erucate | 0.5-3 |
| Dimethiconol | 0.1-10 |
| 3,4,5-(2,4,6 octatrienoyl) gallic acid | 0.03-3 |
| Octyldodecanol | 0.01-1 |

Example 13

Cream Treatment

| Component (INCI name) | Amount w/w (%) |
|---|---|
| Propylene glycol | 0.5-7 |
| Pentylene glycol | 1-3 |
| Steareth-21 | 0.1-3 |
| Steareth-2 | 0.1-3 |
| Caprylic/capric triglyceride | 1-10 |
| Cyclopentasiloxane | 0.5-20 |
| Cetearyl alcohol | 0.01-2 |
| Octyldodecanol | 0.1-5 |
| Disodium EDTA | 0.01-0.1 |
| Beta-sitosteril-2.4.6-octatrienoate | 0.2-4 |
| Phenoxyethanol | 0.8-1 |
| Sodium hydroxide | 0.001-0.2 |
| Citric acid | 0.001-0.3 |

Example 14

Detergent

| Component (INCI name) | Amount w/w (%) |
|---|---|
| Amisoft CS 22 | 4-10 |
| Decyl glucoside | 4-10 |
| Protelan AG 8 (27%) | 4-10 |
| Sodium methyl cocoyl taurate | 4-10 |
| Oxetal VD 92 | 3-8 |
| Antil 127 | 1-2 |
| Cosmocil CQ | 1-2 |
| Citric acid | 1-2 |
| Parfum Green Water 4883 SSA PR15058 | 0.5-1 |
| Ethylhexylglycerin | 0.5-1 |
| PEG-10 Olive glycerides | 0.5-1 |
| Sodium hydroxymethylglycinate | 0.5-1 |
| Ammonium glycyrrhizinate | 0.1-0.3 |
| Panthenol | 0.1-0.3 |
| Zinc PCA | 0.1-0.3 |
| 3,4-dioctatrienoyl caffeic acid | 0.1-2.5 |
| Butyl hydroxyanisole (BHA) | 0.1-0.02 |
| Dipotassium glycyrrhizate | 0.1-0.02 |
| Furalglucitole | 0.1-0.02 |
| Sodium Hydroxide | 0.1-0.02 |
| Water | 50-75 |

DESCRIPTION OF THE DRAWINGS

FIG. 1 shows the results obtained for the compounds of the invention in the MTT assay with induced oxidative stress.

FIG. 2 shows the results obtained for the compounds of the invention in the in vitro TNF-α inflammation test on human keratinocytes NCTC2544.

1) MTT ASSAY WITH INDUCED OXIDATIVE STRESS

Figure 1:
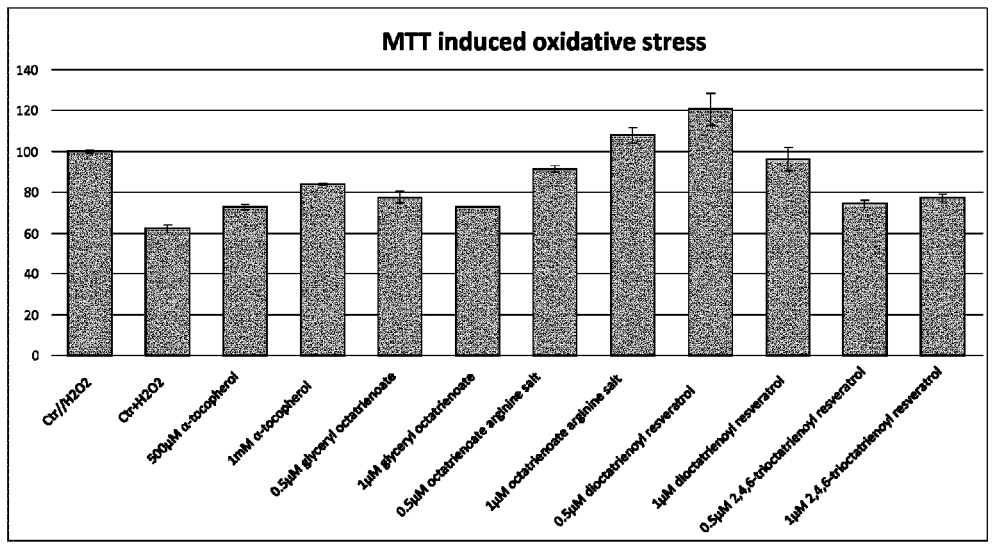
FIGS. 1 and 2 of the accompanying drawings show graphs drawn from experimental studies as described below.

This assay is used to assess the decrease in cell viability using the chromogen oxidizing agent MTT (methylthiazolyldiphenyl-tetrazolium bromide), corresponding to a polycyclic system ($C_{18}H_{16}BrN_5S$) bearing a tetrazole ring that can be easily reduced by the mitochondrial dehydrogenase or by other electron transport systems, thus leading by ring opening to a chromogen nitrogen compound called formazan, whose characteristic functional group is $R^1NH-N=CR^2-N=NR^3$. In the intracellular environment, said formazan forms insoluble crystals to which the membranes are substantially impermeable: the molecule is therefore allowed to entry the cell, but not to exit it, if the molecule is correctly metabolized, i.e. if the electron transport chains are still metabolically active (that is equipped with an active reducing power).

This assay measures the viability of cells subjected to oxidative stress, and is therefore interpreted not only as an indicator of the antioxidant activity but also as an indicator of protection from oxidative stress and enhancement of cellular antioxidant defenses, in general terms being the test non-specific.

With the transformation of MTT, a change in color of the molecule from yellow to dark blue-violet is seen; therefore, to estimate the number of active mitochondria and, therefore, the number of viable cells in the sample, a colorimetric assay with a spectrophotometer read-out is used.

The protocol described below is used as a screening tool for the activity of the compounds of the invention object of the study, after induction of oxidative stress in the human keratinocytes cell line NCTC2544 through application of 1 mM hydrogen peroxide, according to a specific bibliographic reference (Rajapakse et al., 2004). The assay was conducted according to the method described by Coda and collaborators, with some modifications The NCTC 2544 human keratinocytes were seeded in a 96-well plate at a density of $5*10^4$ cells/well and incubated at 37° C. and 5% $CO_2$, until reaching approximately 80% confluence.

The cells were then pretreated for 16 hours with the compounds of the invention to be tested in different concentrations, and with α-tocopherol, tested at the 500 mM and 1 mM concentrations, as a reference. Cells treated with 1 mM $H_2O_2$ were used as negative control; however, cells maintained in culture in complete medium, served as the positive control.

At the end of the 16 hours of pre-treatment, the cells were washed with 1×PBS and incubated for 90 minutes with a 1 mM $H_2O_2$ solution (Sigma-Aldrich, St. Louis, Mo., USA) in serum-free medium at 37° C. and 5% $CO_2$, in the dark.

Once the oxidative stress induction phase was completed, the evaluation of cell viability of the various samples was carried out, according to the method previously described (MTT assay).

The data were expressed as the percentage of cell viability compared to not stressed control cells (ctr), according to the following formula:

% cell viability/ctr=(Abs sample/Abs ctr)*100

All analyzes were performed at least twice in duplicate.

The graph of FIG. 1 summarizes the results obtained for the following compounds of the invention:

glycerol tri-octatrienoate, at the concentration of 0.5 µM and 1 µM octatrienoic acid arginine salt, at the concentration of 0.5 µM and 1 µM resveratrol di-octatrienoate, at the concentration of 0.5 µM and 1 µM resveratrol tri-octatrienoate, at the concentration of 0.5 µM and 1 µM

2) IN VITRO INFLAMMATION TEST ON NCTC 2544 HUMAN KERATINOCYTES EXPERIMENTAL PROCEDURE

A immortalized line of NCTC 2544 human keratinocytes (Perry V. P. et al., 1957), kept in culture in sterile flasks (25 cm$^3$), incubated at 37° C. in a humid atmosphere with 5% $CO_2$ in MEM (Minimum Essential Medium) culture medium added with 10% fetal bovine serum (FBS), 2 mM glutamine, 1% non-essential amino acids, in the presence of 1% of penicillin and streptomycin, is used.

Day 1: Cells Seeding

When the cells (NCTC 2544 human keratinocytes) reached approximately 80% confluence, they were detached with trypsin/EDTA and seeded at a density of 1×10$^6$ cells/ml in 12-well plates, and then incubated at 37° C., 5% $CO_2$ (24 h).

Day 2: Exposure to the Active Compounds to be Tested for 24 h

The active compounds of the invention to be tested were dissolved in DMSO (100%) at a concentration of 10 mM (stock solution), and then diluted in EMEM medium, supplemented with 2.5% FBS, 2 mM L-glutamine, 1% solution NEAA and 1% penicillin (10,000 U/ml)/streptomycin (10,000 pg/ml).

The controls containing culture medium only (negative control) and the culture medium plus LPS (5 μg/ml) (positive control) were included in each plate.

The cells were exposed to a 5 μM concentration of the active compounds to be tested. To each well (except in the negative control) LPS at a concentration of 5 μg/ml was added. Each compound was tested in replicates.

Real-Time qPCR

The activity of the compounds under study on TNF-α gene expression was assessed by relative quantitative RT-PCR (quantitative reverse transcription-polymerase chain reaction-qRT-PCR).

This analysis required 3 sequential steps:
total RNA extraction;
reverse transcription into cDNA;
qRT-PCR.

Extraction of Total RNA from NCTC 2544 Human Keratinocytes

Total RNA was extracted from NCTC 2544 cells by using Tri Reagent (Sigma Aldrich) as described by Chomczynski and Mackey [132].

Use of Tri Reagent is a fast, efficient and cost effective method for the extraction of the total RNA or for the simultaneous extraction of RNA, DNA and proteins from human samples. The isolated RNA can be used for a variety of analyses including RT-PCR.

The entire procedure can be completed in 1 hour and the recovery of not degraded messenger RNA is 30-150% more compared to other methods.

After incubation with the active compounds of interest, the cells were washed with PBS (1×) and finally lysed with Tri Reagent. Each lysate was transferred to an Eppendorf and was further homogenized with an insulin syringe. To the lysates chloroform (200 μL) was then added, and they were vortexed and left to stand at room temperature for 15 minutes.

After centrifugation at 12,000×g, at 4° C. for 15 minutes, for each lysate 3 phases were obtained: an organic phase containing the proteins and cellular elements, a middle phase containing the DNA (visible as a white ring) and an aqueous phase (colorless) containing the RNA. The aqueous phases were treated with isopropanol and the samples were allowed to stand overnight. The samples were centrifuged at 12,000×g, at 4° C. for 10 minutes. The supernatant was removed and the pellets washed with sterile 75% ethanol and centrifuged again at 7,500×g, at 4° C. for 5 minutes. The pellets were then resuspended with 20 μL of water DEPC (diethylpyrocarbonate-treated) and placed in a thermostatic digital bath (Swbd-STUART) at 56° C. for 15 minutes.

With the use of a spectrophotometer (Jenway UV/VIS MOD: 6715, BS-6715B0), the μg/mL concentrations of the total RNA extracted were calculated, at a wavelength of 260 nm.

Finally, the RNA integrity (2 μg/mL) was evaluated by means of an electrophoretic run on 1% agarose gel.

Reverse Transcription into cDNA

The total RNA was converted into cDNA (complementary DNA), using an enzyme capable of synthesizing a DNA molecule using a RNA strand as a mold; this RNA dependent-DNA polymerase enzyme is called reverse transcriptase.

It binds to the 3' end of a single-stranded RNA and synthetize the cDNA strand using random primers and deoxynucleotide triphosphate (DNTP).

For this purpose, a "High-Capacity cDNA Reverse Transcription Kit" commercial kit (Applied Biosystems, Monza, Italy) containing RT Buffer 10×, DNTP 25×, Random Primers 10×, Multi Scribe and water DEPC was used.

The RNA extracted and quantified was diluted at a concentration of 2 μg/mL and reverse-transcribed into cDNA. A 10 μL Master Mix (containing RT Buffer 10×, DNTP 25×, Random Primers 10×, Multi Scribe and water DEPC) was prepared, to which 10 μL of RNA (2 μg/mL) were added.

The samples were placed into a thermocycler (Stratagene Mx3000P Real Time PCR System, Agilent Technologies Italia S.p.A., Milano, Italy) and subjected to reverse transcription in the following conditions:
25° C. for 10 minutes;
37° C. for 120 minutes;
85° C. for 1 minute;
25° C. for 2 minutes.

At the end of reverse transcription, to the samples 30 μL of water DEPC were added to obtain a final concentration of cDNA of 40 ng/μL.

qRT-PCR.

qRT-PCR is a method of amplification and quantification of the amplified products in real time, by monitoring the fluorescence emitted during the reaction.

For the RT-PCR amplification, the TaqMan® probes system (Applied Biosystems) was used. The following TaqMan probes were used: Hs00998133_m1(TNF-α) and Hs999999_m1 (GAPDH). As a control gene (housekeeping) GAPDH (human glyceraldehyde-3-phosphate dehydrogenase) was used.

The Taqman probe is a type of probe that allows the development of fluorescence while the amplification advances. A reporter (FAMTM fluorophore) is bonded to its 5' end, while at its 3' end there is a quencher. The proximity between the reporter and the quencher delete the emission of the fluorescence signal. The fluorescence is detected only in the presence of 5' exonuclease activity of the thermostable DNA polymerase (Taq polymerase), and the accumulation of the amplification products can be evaluated by the increase of reporter fluorescence which increases during each cycle.

For the qRT-PCR, a Master Mix was prepared as follows:
10 μL of "2× TaqMan Universal PCR Master Mix" (containing AmpliTaq Gold DNA Polymerase, UNG AmpErase®, dNTPs with dUTP, Passive reference Rox II, optimized Buffer);

1 μL "20× TaqMan Gene Expression Assays" (containing 2 primers and the fluorescent probe labeled with FAMTM fluorophore);

5 μL of water DEPC.

To the Master Mix, 4 μL of cDNA for the target gene target and 1 μL of cDNA for the housekeeping gene were added.

The amplification was performed under the following conditions:

50° C. for 2 minutes (UNG AmpErase ® activation);
95° C. for 10 minutes (TaqMan polymerase activation);
95° C. for 15 seconds (denaturation);  } 40 cycles
60° C. for 1 minute (annealing-extension).

Each analysis was performed in triplicates.

The data obtained were analyzed according to the 2-ΔΔCt [133] method, and it was thus possible to calculate the relative values of expression of the gene of interest, normalized vs the housekeeping gene e calibrated on the control sample (untreated cells):

ΔΔCt=ΔCt$_{target-housekeeping}$(control)−
ΔCt$_{target-housekeeping}$(treated cells)

2-ΔΔCt was calculated assuming an amplification efficiency of 100%.

Figure 2:
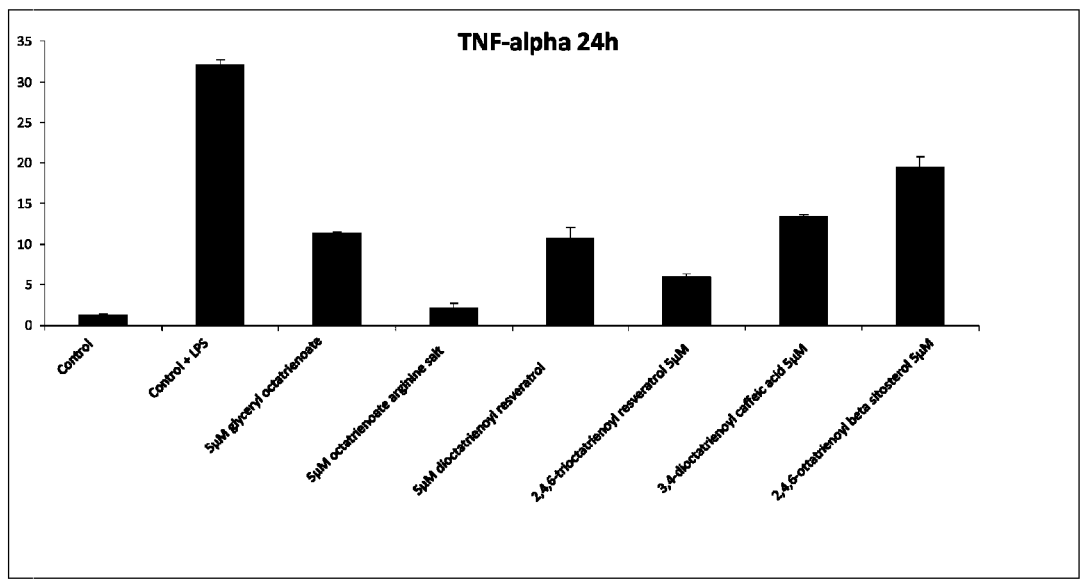

The graph of FIG. 2 summarizes the TNF-α results over 24 hours, obtained for the following compounds of the invention:

glycerol tri-octatrienoate, at a concentration of 5 μM
octatrienoic acid arginine salt, at a concentration of 5 μM
resveratrol di-octatrienoate, at a concentration of 5 μM
resveratrol tri-octatrienoate, at a concentration of 5 μM
caffeic acid 3,4-di-octatrienoate, at a concentration of 5 μM
sitosterol octatrienoate, at a concentration of 5 μM A comparative examination of the graphs of FIG. 1 and FIG. 2 shows that the compounds of the invention are suitable for use in therapeutics and cosmetics for topical application on the skin or on the scalp for obtaining a combined antioxidant activity against ROS combined with an anti-inflammatory action, for opposing at the same time the oxidizing action of free radicals, that can be exerted together with inflammatory effects, in order to preserve the physiological conditions of the human epidermis and preserve the physiological conditions of the hair, thus their state of health, particularly under the combined action of these harmful agents.

For what concerns the graph of FIG. 1, the comparison with the reference compound α-tocopherol (tested at a concentration of 500 μM and 1 mM) generally shows an increase of cells viability (% viability), thus a higher antioxidant activity, for the compounds of the invention, and in particular a surprising antioxidant activity, for example for the octatrienoic acid arginine salt (91.5% viability) and resveratrol di-octatrienoate (120.5% viability) at the lower concentration of 0.5 μM compared to α-tocopherol.

It has also to be noted that at that 0.5 μM concentration, both resveratrol and octatrienoic acid, as such, in the same MTT assay have a result of % viability of approximately 75, so that the increase in antioxidant activity shown in FIG. 1 for resveratrol di-octatrienoate (120.5% viability) appears remarkable not only compared to the reference comparison α-tocopherol, but also with respect to the individual acid and alcohol from which the ester of the invention originates.

As defined above, the MTT assay measures the viability of cells subjected to oxidative stress and is, therefore, interpreted non only as an indicator of antioxidant activity, but also as an indicator of protection against oxidative stress and of cellular antioxidant defenses enhancement, in general terms as the test is nonspecific.

For the same compounds of the invention, in addition to this antioxidant activity, the graph of FIG. 2 shows also a surprising anti-inflammatory activity, an activity that, for example, resveratrol as such proves not to have, if subjected to the same TNF-α assay.

The invention claimed is:

1. 2,4,6-octatrienoic acid derivative compound having general formula (I)

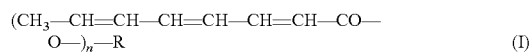
(CH$_3$—CH=CH—CH=CH—CH=CH—CO—O—)$_n$—R  (I)

consisting of esters, wherein n=1, 2, 3 and wherein R is selected from (i) an alkyl of a polyol, phenol, or phenolic acid, (ii) an aryl of a polyol, phenol, or phenolic acid, or (iii) a cycloalkyl of a polyol, phenol or phenolic acid; or consisting of an arginine salt wherein n=1 and R=H; with the proviso that, when n=1, R is not 2,3-dihydroxy propyl.

2. Compounds according to claim 1, characterized in that said polyol, phenol or phenolic acid is selected from glycerol, sitosterol, resveratrol, caffeic acid, ferulic acid, gallic acid.

3. Compounds according to claim 1, characterized in that they are selected from the following: caffeic acid 3,4-di-octatrienoate, sitosterol octatrienoate, resveratrol octatrienoate, resveratrol di-octatrienoate, resveratrol tri-octatrienoate, glycerol tri-octatrienoate, octatrienoic acid arginine salt, ferulic acid octatrienoate, octatrienoic ferulic 4-(2,4,6-octatrienoyl)anhydride, gallic acid tri-octatrienoate.

4. A pharmaceutical or cosmetic composition, wherein the active ingredient is a compound of general formula (I)

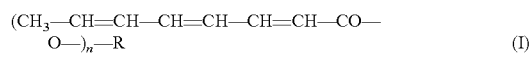
(CH$_3$—CH=CH—CH=CH—CH=CH—CO—O—)$_n$—R  (I)

consisting of esters, wherein n=1, 2, 3 and wherein R is selected from (i) an alkyl of a polyol, phenol, or phenolic acid, (ii) an aryl of a polyol, phenol, or phenolic acid, or (iii) a cycloalkyl of a polyol, phenol, or phenolic acid; or consisting of an arginine salt wherein n=1 and R=H.

5. The composition according to claim 4, wherein a compound of general formula (I) is used as the active ingredient formulated with excipients for topical application to the skin for obtaining a combined antioxidant activity against free radicals together with an anti-inflammatory action.

6. The composition according to claim 4, wherein a compound of general formula (I) is used as the active ingredient formulated with excipients for topical application to the scalp for obtaining a combined antioxidant activity against free radicals together with an anti-inflammatory action.

7. The composition according to claim 4, characterized in that said polyol, phenol or phenolic acid is selected from glycerol, sitosterol, resveratrol, caffeic acid, ferulic acid, gallic acid.

8. The composition according to claim 4, characterized in that said compound is selected from the following: caffeic acid 3,4-di-octatrienoate, sitosterol octatrienoate, resveratrol octatrienoate, resveratrol di-octatrienoate, resveratrol tri-octatrienoate, glycerol tri-octatrienoate, octatrienoic acid arginine salt, ferulic acid octatrienoate, octatrienoic ferulic 4-(2,4,6-octatrienoyl)anhydride, gallic acid tri-octatrienoate.

9. The composition according to claim 4, wherein said active ingredient is a mixture of two or more of the compounds of formula (I).

10. The composition according to claim 4 comprising said active ingredient in an amount in the range between 0.5 µM and 0.1 mM.

11. The composition according to claim 4, comprising said active ingredient in amounts expressed as parts by weight, w/w (%), within the following ranges: 0.01-2.5; 0.1-2.5; 0.2-2.5; 0.01-1.5; 0.1-2; 0.2-2; 0.03-3; 0.2-4.

* * * * *

UNITED STATES PATENT AND TRADEMARK OFFICE
CERTIFICATE OF CORRECTION

PATENT NO. : 9,738,682 B2  
APPLICATION NO. : 15/124273  
DATED : August 22, 2017  
INVENTOR(S) : Giuliani et al.

Page 1 of 1

It is certified that error appears in the above-identified patent and that said Letters Patent is hereby corrected as shown below:

In the Claims

In Claim 1, at Column 20, Line 23, please delete "R=H" and insert --R=H--

In Claim 4, at Column 20, Line 46, please delete "R=H" and insert --R=H--

Signed and Sealed this  
Twenty-sixth Day of June, 2018

Andrei Iancu  
*Director of the United States Patent and Trademark Office*